United States Patent [19]

Huber et al.

[11] Patent Number: 5,723,612
[45] Date of Patent: Mar. 3, 1998

[54] PROCESS FOR THE PREPARATION OF PURE 4,6-DIHLOROPYRIMIDINE

[75] Inventors: Wolfgang Huber, Salzburg; Franz Thomas Schwarz, Wolfern; Ferdinand Heu, Linz, all of Austria

[73] Assignee: DSM Chemie Linz GmbH, Linz, Austria

[21] Appl. No.: 657,301

[22] Filed: Jun. 3, 1996

[30] Foreign Application Priority Data

Jun. 2, 1995 [AT] Austria ..................... 939/95

[51] Int. Cl.$^6$ .................................. C07D 239/02
[52] U.S. Cl. ...................................... 544/334
[58] Field of Search ............................. 544/334

[56] References Cited

U.S. PATENT DOCUMENTS 5,525,724  6/1996  Hunds ........................ 544/334
5,563,270  10/1996  Schwarz et al. ............. 544/330

OTHER PUBLICATIONS

I. Wempen et al., *J. Org. Chem.,* 6, 688–691 (1963).

B. Feit et al., *J. Heterocycl. Chem.,* 11, 295–297 (1974).

G. Kenner et al., *J. Chem. Soc.,* 574–575 (1943).

*Primary Examiner*—Mukund J. Shah
*Assistant Examiner*—Brenda Coleman
*Attorney, Agent, or Firm*—Wenderoth, Lind & Ponack

[57] ABSTRACT

Process for the preparation of pure 4,6-dichloropyrimidine by reaction of 4,6-dihydroxypyrimidine with an excess of phosphorus oxychloride at 20° C. up to reflux temperature, in the presence of a trialkylamine as acid scavenger and catalyst.

9 Claims, No Drawings

PROCESS FOR THE PREPARATION OF PURE 4,6-DIHLOROPYRIMIDINE 4,6-dichloropyrimidine (DCP) is a known and valuable intermediate for medicaments and agrochemicals. Some processes for the preparation of DCP have accordingly already been disclosed in the literature.

Thus, for example, J. Chem. Soc (1943) p. 575, and J. Chem. Soc. (1951) p. 2214 describe a process in which 4,6-dihydroxypyrimidine (DHP) is reacted under reflux with an excess of phosphorus oxychloride and dimethylaniline as acid scavenger to form DCP. DCP is isolated, after distilling off excess phosphorus oxychloride, by pouring the mixture onto ice water with subsequent extraction with ether. The extract thus obtained is then washed with a sodium carbonate solution, dried and concentrated by evaporation. The yields in these processes are 75.2% and, after subsequent distillation or recrystallization, 51.3%. However, in this process, large amounts of the hydrolysis product 4-chloro-6-hydroxypyrimidine are formed in the work-up by pouring the reaction mixture onto ice water, which greatly reduces the yield of DCP and also its purity and necessitates an additional purification step. A further problem in this process is the manner in which DCP is dried, since the latter sublimes readily owing to its high vapor pressure.

The object of the present invention was therefore to find a simple process for the preparation of pure 4,6-dichloropyrimidine. Unexpectedly, this object has been achieved by the process according to the invention.

The present invention therefore relates to a process for the preparation of pure 4,6-dichloro-pyrimidine by reaction of 4,6-dihydroxypyrimidine with an excess of phosphorus oxychloride in the presence of an acid scavenger and catalyst, which comprises using a trialkylamine having 2 to 4 C atoms in the alkyl moiety as acid scavenger and catalyst.

In the process of the invention, 4,6-dihydroxypyrimidine (DHP) is reacted with an excess of $POCl_3$ to form 4,6-dichloropyrimidine. DHP is suspended for this purpose in $POCl_3$, which serves both as reagent and as reaction medium. The ease of handling of the suspension is determined by the amount of $POCl_3$ used. The molar ratio of DHP to $POCl_3$ can vary here, the lower limit being influenced by the stirrability of the suspension and the upper limit being principally influenced by economic factors. Preferably, a molar ratio of DHP to $POCl_3$ of about 1:3 to 1:8 is used, particularly preferably from about 1:4 to 1:6. A greater excess of $POCl_3$ has no disadvantageous effects on the reaction and can also be used if desired, but is generally not expedient for economic reasons. To this suspension is added a trialkylamine having 2 to 4 C atoms in the alkyl moiety. Suitable trialkylamines in this case are triethylamine, tri-n-butylamine and tripropylamine. Preferably, triethylamine is used. The trialkylamine is preferably added over a period of about 20 to 240 minutes, particularly preferably from 60 to 150 minutes, as a result of which the temperature, depending on the addition rate and dilution, can increase up to the reflux temperature, but is preferably added at such a rate that the temperature does not increase above 90° C. The amount of added tri-alkylamine can vary here, so that, based on the amount of HCl eliminated in the reaction, a molar deficit, an equimolar amount or else a molar excess of trialkylamine can be used. However, preferably, a molar ratio of DHP to trialkylamine of about 1:2 to 1:3 is used, particularly preferably up to 1:2.25. After addition is completed, the reaction mixture thus obtained is heated, if necessary, to a temperature up to 100° C. and kept at this temperature for about 10 to 300 minutes, preferably about 20 to 90 minutes.

Preferably, the reaction mixture is kept at a temperature of 40° to 95° C., particularly preferably 65° to 90° C.

For the isolation and workup of DCP, excess $POCl_3$ is distilled off. Preferably, distillation is performed under vacuum. The bottom temperature can vary as a function of the vacuum achieved, the lower limit being influenced by the stirrability of the reaction mixture. Advantageously, the remaining residue, simultaneously with a neutralizing agent, preferably with sodium hydroxide solution or potassium hydroxide solution, particularly preferably with 20 to 50% strength sodium hydroxide solution, is introduced into water at a temperature of about 30° to 70° C., the rate of the addition being varied in such a manner that a pH as constant as possible between 2 and 5, preferably from about 2 to 3, is achieved and the temperature does not increase above 70° C. The mixture is then further stirred for about 10 to 60 minutes at a temperature between about 30° and 70° C., preferably between 40° and 50° C., and the reaction mixture is cooled to a temperature between about 10° and 30° C., whereupon DCP precipitates out. Further workup can then be performed by filtering off, washing with water and drying at about 40° C. in vacuo. For further purification, DCP can, if desired, be further purified by distillation. However, after the washing with water, DCP can also be extracted with an inert and water-immiscible or virtually water-immiscible solvent, which is prewarmed to about 50° to 65° C., and, after separating off the aqueous phase, can be isolated from the solvent phase by fractional vacuum distillation. Suitable solvents in this case are, preferably, toluene, xylenes, cyclohexane or ether, such as methyl tert-butyl ether, diisopropyl ether, or mixtures thereof.

A further possibility is that the precipitated DCP, without prior filtration and washing, is extracted directly from the reaction solution with the inert solvent and again obtained by fractional vacuum distillation.

By means of the process according to the invention, DCP is obtained in high purity (up to 99.9%) compared with the prior art, and in yields of over 80%.

EXAMPLE 1

90 g (0.80 mol) of 4,6-dihydroxypyrimidine and 592.0 g (3.86 mol) of phosphorus oxychloride were introduced into a 500 ml jacketed glass reactor equipped with agitator, reflux condenser and thermostat heater and 167.7 g (1.65 mol) of triethylamine were added in the course of 120 minutes. After completion of the triethyl-amine addition, the reaction mixture was heated to 85° C. and kept at this temperature for 30 minutes.

Excess phosphorus oxychloride was then distilled off in vacuo. 500 ml of water which had been preheated to 40° C. was introduced into a further reaction vessel, into which water the reaction solution and 50% strength sodium hydroxide solution were simultaneously added. The two solutions (i.e. the reaction mixture from the chlorination and the sodium hydroxide solution) were introduced into the water at a rate such that the pH was kept as constant as possible at pH 2.5 and the temperature did not increase above 53° C.

After completion of the addition, the mixture was stirred for a further 30 minutes at 45° C. The reaction mixture was then cooled to 15° C., the product was filtered off, washed 3× each time with 200 ml of water, and dried in vacuo at 40° C.

Yield: 106.2 g of 4,6-dichloropyrimidine (=89.1% of theory)

Analyses: content (HPLC): 98.6% w/w.

By extracting the mother liquor with toluene, a further 3.2 g (=2.7% of theory) of 4,6-dichloro-pyrimidine could be obtained.

EXAMPLE 2

90 g of DHP were reacted with 592 g of $POCl_3$ in the presence of 167.7 g of triethylamine similarly to Example 1.

Work-up was likewise performed similarly to Example 1, up to cooling the reaction mixture.

The precipitated product was then filtered off and washed only 1× with 200 ml of water.

The filter-moist product was then washed from the filter funnel with 400 ml of toluene heated to 60° C. After separating off the aqueous phase in a separating funnel, the toluene solution of 4,6-dichloropyrimidine was fractionally distilled in vacuo.

Yield:

100.4 g of DCP (=84.3% of theory) Content (GC): 99.9% w/w

What we claim is:

1. A process for the preparation of pure 4,6-dichloropyrimidine by reaction of 4,6-dihydroxypyrimidine with an excess of phosphorus oxychloride in the presence of an acid scavenger and catalyst, which comprises using a trialkylamine having 2 to 4 C atoms in the alkyl moiety as acid scavenger and catalyst and isolating 4,6-dichloropyrimidine by distilling off excess phosphorus oxychloride and adding the residue and a neutralizing agent simultaneously to water at 30° to 70° C. so that a pH between 2 and 5 is achieved, whereupon, after stirring for 10 to 60 minutes and subsequent cooling to 10 to 30° C., 4,6-dichloropyrimidine precipitates out.

2. The process as claimed in claim 1, wherein the trialkylamine used is triethylamine.

3. The process as claimed in claim 1, wherein 4,6-dihydroxypyrimidine and phosphorus oxychloride are used in a molar ratio of 1:3 to 1:8.

4. The process as claimed in claim 1, wherein the trialkylamine and 4,6-dihydroxypyrimidine are used in a molar ratio of 2:1 to 3:1.

5. The process as claimed in claim 1, wherein the neutralizing agent used is sodium hydroxide solution or potassium hydroxide solution.

6. The process as claimed in claim 1, wherein said pH is between 2 and 3.

7. The process as claimed in claim 1, wherein the precipitated 4,6-dichloropyrimidine is filtered off, washed with water and dried in vacuo.

8. The process as claimed in claim 1, wherein the precipitated 4,6-dichloropyrimidine is, after filtration and washing with water, extracted with an inert water-immiscible or substantially water-immiscible solvent and fractionally distilled in vacuo.

9. The process as claimed in claim 8, wherein the inert water-immiscible or substantially water-immiscible solvent used is toluene, xylenes, ethane or cyclohexane, or mixtures thereof.

* * * * *